(12) United States Patent
Martz et al.

(10) Patent No.: US 11,232,397 B2
(45) Date of Patent: Jan. 25, 2022

(54) SYSTEMS AND METHODS FOR CONTROLLING PRODUCTION AND DISTRIBUTION OF CONSUMABLE ITEMS BASED ON THEIR CHEMICAL PROFILES

(71) Applicant: PENROSE HILL, New York, NY (US)

(72) Inventors: Matthew K. Martz, Chapel Hill, NC (US); Erik Steigler, New York, NY (US); Philip James, New York, NY (US)

(73) Assignee: Penrose Hill, New York, NY (US)

( * ) Notice: Subject to any disclaimer, the term of this patent is extended or adjusted under 35 U.S.C. 154(b) by 182 days.

(21) Appl. No.: 16/431,346

(22) Filed: Jun. 4, 2019

(65) Prior Publication Data
US 2019/0370736 A1   Dec. 5, 2019

Related U.S. Application Data

(60) Provisional application No. 62/680,229, filed on Jun. 4, 2018.

(51) Int. Cl.
*G06Q 10/08* (2012.01)
*G01N 33/14* (2006.01)

(52) U.S. Cl.
CPC ......... *G06Q 10/087* (2013.01); *G01N 33/146* (2013.01)

(58) Field of Classification Search
None
See application file for complete search history.

(56) References Cited

U.S. PATENT DOCUMENTS

| | | | | |
|---|---|---|---|---|
| 10,783,507 B1* | 9/2020 | Votolato | ................ | G06Q 20/20 |
| 10,825,567 B1* | 11/2020 | Wala | .................... | G16H 40/63 |
| 10,878,458 B2* | 12/2020 | Lee | .................... | G06F 16/9535 |
| 2008/0147489 A1* | 6/2008 | Groman | ................ | G06Q 30/02 |
| | | | | 705/14.66 |
| 2009/0259344 A1* | 10/2009 | Watson | ................ | G06Q 10/08 |
| | | | | 700/283 |
| 2018/0315111 A1* | 11/2018 | Alvo | .................... | G06Q 10/087 |
| 2019/0392378 A1* | 12/2019 | Alvo | .................... | G06Q 10/087 |
| 2020/0029133 A1* | 1/2020 | Gehlsen | ............ | H04N 21/8549 |
| 2020/0074517 A1* | 3/2020 | Meier | ................ | G06Q 30/0282 |
| 2020/0080980 A1* | 3/2020 | Clark-Joseph | ....... | G06Q 30/018 |
| 2020/0184530 A1* | 6/2020 | Anderson | ............. | A23G 9/322 |
| 2020/0264168 A1* | 8/2020 | Post | ................ | G01N 33/54326 |

* cited by examiner

*Primary Examiner* — Fateh M Obaid
(74) *Attorney, Agent, or Firm* — Buckley, Maschoff & Talwalkar LLC

(57) ABSTRACT

Embodiments of the present invention relate to a platform for controlling production and distribution of consumable items based on machine learning processes derived from chemical profiles of the consumable items.

12 Claims, 8 Drawing Sheets

SYSTEMS AND METHODS FOR CONTROLLING PRODUCTION AND DISTRIBUTION OF CONSUMABLE ITEMS BASED ON THEIR CHEMICAL PROFILES

CROSS REFERENCE TO RELATED APPLICATION

This application claims the benefit of U.S. Provisional Patent Application No. 62/680,229 filed on Jun. 4, 2019, the contents of which are hereby incorporated by reference for all purposes.

FIELD OF THE INVENTION

The disclosed embodiments are directed to controlling production and distribution of consumable items based on machine learning processes derived from chemical profiles of the consumable items.

BACKGROUND

Conventionally, consumable items wine recommendations may be based on tasting by a wine expert who may qualitatively evaluate the characteristics of a wine using terminology, such as, for example, full bodied, spicy, earthy, etc. Such terms are inherently qualitative and subjective.

SUMMARY

In one aspect, the disclosed embodiments provide a platform for controlling production and distribution of consumable items based on machine learning processes derived from chemical profiles of the consumable items. The consumable item may be wine, e.g., bottles of wine distributed via a website store or wine club. Panels of raw chemical analysis of the wines may be obtained in a laboratory and these may provide a number of attributes, such as, pH, panels of organic acids, etc. The chemistry panel data may be used to build a user level model which may be used, for example, to establish a user taste profile and provide recommendations to the user via a website. The chemistry panel data may also be used to build Gaussian Mixture Models (GMM) which are a form of machine learning. A GMM model may be used to look at distributions of subsets of data and generate novel data that fits well within a given distribution. Such models can be used to create "algorithmic" products, e.g., algorithmic wines. Deep learning models may be used to build neural networks to perform functions such as generating wine labels and performing high-dimensional product (e.g., wine) clustering. The chemistry panel data may be input into dynamic time warping (DTW) alignment calculations which perform mathematical operations to determine how different the chemistry vectors are from one another. The results may be used to build a model of spatial ranking (SR), which is stored. DTW can be used to align vectors which are non-linear and widely distributed and collapse them into the same vector space. This includes calculating an energy cost to collapsing the vectors into the same space, i.e., a measure of how different the vectors are from one another.

Figure 1:
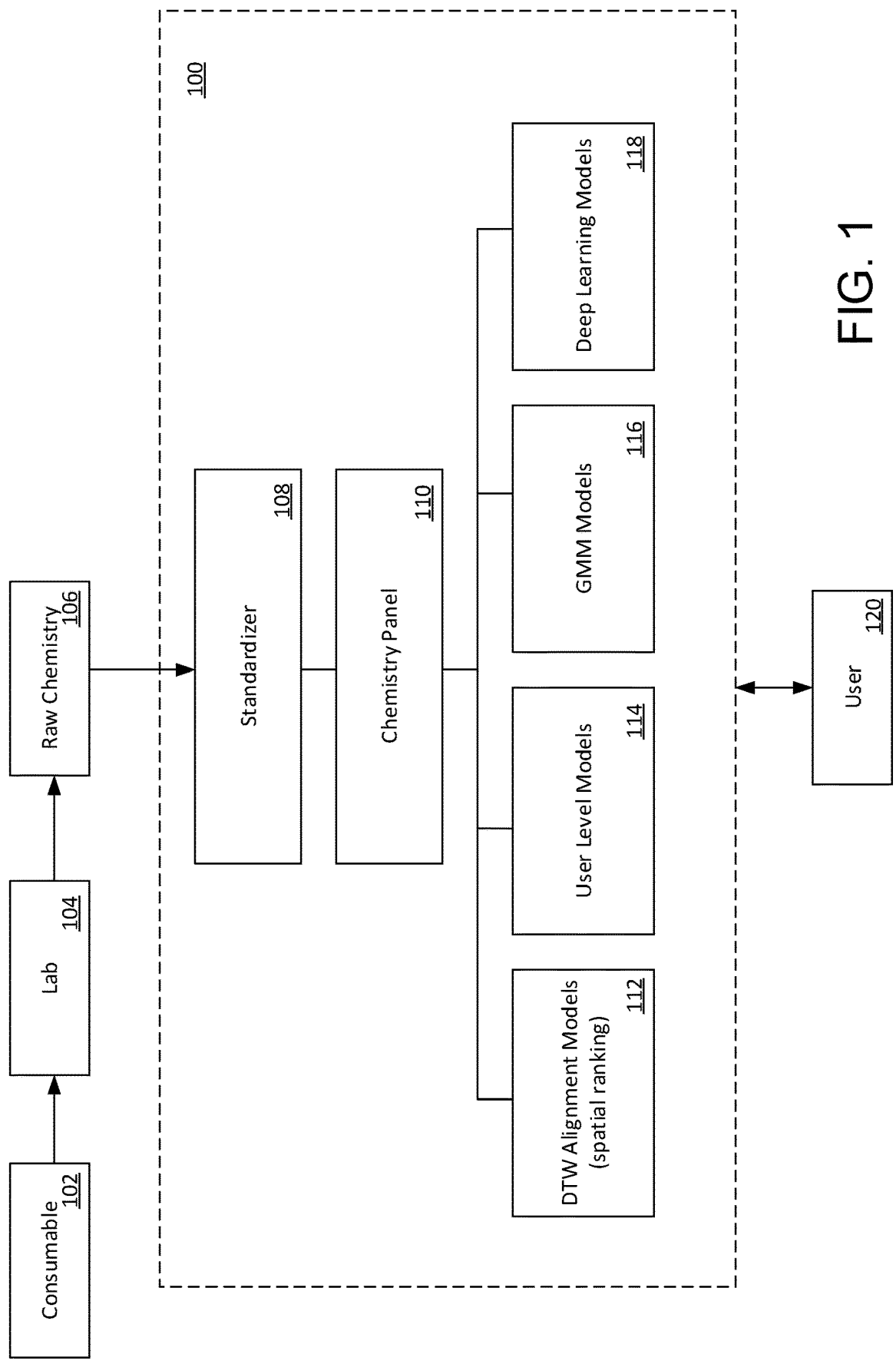
FIG. 1 is a diagram depicting data input to a platform for controlling production and distribution of consumable items based on machine learning processes derived from chemical profiles of the consumable items.

Throughout the drawings and the detailed description, unless otherwise described, the same drawing reference numerals will be understood to refer to the same elements, features, and structures. The relative size and depiction of these elements may be exaggerated or adjusted for clarity, illustration, and/or convenience.

DETAILED DESCRIPTION

FIG. 1 is a diagram depicting a platform 100 for controlling production and distribution of consumable items based on machine learning processes derived from chemical profiles of the consumable items. The diagram provides a top-level view of the platform 100 focusing on the data that is input into the platform 100, processes used to operate on the data, and aspects of the output of the platform. Pursuant to some embodiments, the platform 100 operates on data associated with consumables 102 (such as, for example, wine including, for example, bottles of wine distributed via a website store, a physical store, or a wine club). For clarity and ease of exposition, wine will be used as the example consumable item throughout the remainder of this disclosure, although those skilled in the art, upon reading this disclosure, will appreciate that features of the present invention may be applied to other types of consumables with desirable results.

Chemical attributes of the consumables 102 are identified using laboratories 104. For example, panels of raw chemical analysis 106 of the wines are obtained in a laboratory 104 and these provide a number of attributes, such as, pH, panels of organic acids, etc. These values are measured and are output in a raw unit form 106. The data may be in the form of a parsable data file, e.g., a CSV file, which is input to the platform 100.

In disclosed embodiments, the raw chemistry data 106 may be stored on a lab results portal and exported in bulk as a CSV file. Alternatively, the raw chemistry data 106 output of the lab results portal may be integrated into a database such as a wine production database (not shown in FIG. 1, but which may be a part of, or accessible to the platform 100). For example, there may be an application program interface (API) which pushes the measured chemical data 106 directly into the database. The raw chemistry data 106 may be dumped into a command line API or there may be a web-accessible API front end to upload CSV files into the platform 100.

The platform 100 receives the raw chemistry data 106 (e.g., as a CSV file or the like), stores it in memory, and puts it through a standardizer 108 which manipulates the data to make it amenable to the downstream machine learning processes 112, 114, 116, 118. For example, the standardize 108 may perform data manipulation such as standardization, removing the mean and scaling each attribute distribution to unit variance, and other data manipulations to get it into a format that can be used for downstream calculations. In disclosed embodiments, the standardized data is stored as a model object which is stored in a storage location accessible to the machine learning processes 112-118. For example, the model object could be stored as a chemistry panel 110 in a cloud storage location, such as, for example, Amazon S3 Cloud storage, Google Cloud, or the like. In some embodiments, multiple versions of a model object may be provided in different formats (e.g., to accommodate different format requirements of different machine learning processes 112-118).

The chemistry panel 110 data is used in processes which are configured to pull down the chemistry panels 110 for particular wines. In disclosed embodiments, there is a matrix in which lookups can be performed using product stock keeping unit (SKU). For example, each wine may be identified by a SKU, and chemistry panel 110 data may be associated with or linked to each SKU. The resulting vectors are attribute vectors (i.e., chemistry panels) in which each column is a chemical attribute and the value in a particular cell in the vector is the standardized measured value that is converted from the raw chemistry. The standardized chemistry panel matrix is stored in a location accessible to models 112-118 (e.g., such as the cloud storage locations discussed above) and the data can be pulled down as needed. The data can be used in various use cases/modalities, as discussed in further detail below.

In disclosed embodiments, the data 110 may be input into dynamic time warping (DTW) alignment models 112 which perform mathematical operations to determine how different the chemistry vectors are from one another. The results may be used to build a spatial ranking (SR) model, which is stored in a location accessible to the platform 100. DTW alignment models 112 can be used to align vectors which are non-linear and widely distributed and collapse them into the same vector space. For example, pursuant to some embodiments, this may include calculating an energy cost to collapsing the vectors into the same space—that is, a measure of how different the vectors are from one another. DTW alignment models 112 allows the vectors to move in high-dimensional space, can be numerically expedited with algorithms to control the warping window, allows for the application of non-standard local weights, handles comparison vectors of differing length, and can be efficiently scaled with the increase of vector length.

Pursuant to some embodiments, it is possible to keep track, in high-dimensional space, of where the differences are most significant. This results in a raw value, i.e., a unitless value, which can be used to create a "heat map" of vector alignment costs. For example, such a map could have SKU values defining rows and columns. The distance, i.e., alignment cost, between two SKUs can be determined for a particular point in time. As an example, reading down a column of a particular SKU (e.g., a particular wine) would give the range of the alignment cost to all other SKUs for the particular wine. A use case might be, for a given SKU, to obtain the next five most similar wines to the wine associated with the given SKU by yielding from the rank ordered column the next five lowest cost alignment SKUs. For example, a product page of a website "store" may indicate a selection of the five similar wines to one which has been selected by a consumer but which is out of stock. Thus, the wine chemistry can be used to give the user the next closest thing to the desired wine. Conversely, the five highest cost alignment SKUs could be selected to generate a list of SKUs that are least similar.

DTW alignment models 112 are commonly used in finance and audio-visual processing. For example, DTW algorithms can be used to determine how different two waveforms are from one another. In disclosed embodiments, DTW alignment models 112 may be performed using a coded module, e.g., using Python, which includes the necessary mathematical functions to perform the calculations. In disclosed embodiments, a coding (e.g., script) language, such as Python, may be used to code the entire platform. DTW alignment models 112 may be stored, for example, in a Python data format and the pre-computed models may be stored in a storage location accessible to the platform 100 such as the cloud storage locations discussed above.

The chemistry panels 110 can also be used to build a user level model 114 which may be used, for example, to provide recommendations to the user via the website. The chemistry panels may also be used to build Gaussian Mixture Models (GMM) 116 which are a form of machine learning. A GMM model 116 may be used to look at distributions of data and generate novel data that fits well within a given distribution. Such models can be used to create "algorithmic" products, e.g., algorithmic wines. Deep learning models 118 may be used to build neural networks to perform functions such as generating wine labels and performing high-dimensional product (e.g., wine) clustering.

In disclosed embodiments, the DTW models 112, user level models 114, GMM models 116, and deep learning models 118 may be created as a number of separate component modules. Further, while the models are discussed in the plural, individual models may be provided (e.g., a single GMM model). In a specific workflow, particular modules may be called. For example, if new raw chemistry 106 is detected through the front-end API, the standardizer 108 may be invoked to perform standardization operations and then store the resulting chemistry panel 110. The platform 100 may then cause the DTW calculation models 112 to be run to pre-build the model and store it to cloud storage because if there is new chemistry, all of the models should be rebuilt. In disclosed embodiments, the models may be callable by hand, e.g., in a command line, to run specific components. In some embodiments, the platform 100 may automatically call or invoke the models 112-118 as needed (e.g., upon a detected change in raw chemistry 106).

In disclosed embodiments, at least some of the models 112-118 may be incorporated into a single coded element. In one aspect, there may be an autonomous set of algorithms which parse through and pull in correct components to perform functions that need to be performed. This may be driven by a front-end API. For example, if a user recommendation is being sought, a URL endpoint may be called, e.g., with a user ID, and calculations will be run to build a model which generates predictions and returns recommendations for the corresponding user. For example, a user 120 may interact with the platform 100 using, for example, a networked computer in communication with the platform 100. In another aspect, analytics may be employed, e.g., if there is a one-off business intelligence request to make predictions for a particular SKU in a particular region (e.g., California), then specific routines will be pulled in to run particular components to produce the necessary data. In such an embodiment, a user 120 may interact with the platform 100 to define the request for predictions associated with the particular SKU in the particular region. The results may then be provided to the user 120.

In disclosed embodiments, the user level models may be used in a use case involving a wine club. A user (operating a user device 120) may interact with the wine club (e.g., via a wine club website or the like) and may be requesting the next box (e.g., case) of wine. The webpage may show a box, e.g., on a splash page presented by the website, generated by the platform 100 based on information previously provided by (or gathered about) the user. For example, the website may ask the user to rate wine's that have previously been provided to the user. The information about the user's wine ratings may then be used to pull in chemistry to build a user level model 114 and to make predictions on behalf of that user. The user level model 114 may then be used to make predictions on all remaining SKUs (based on their chemistry panels 110) to create a set of next recommendations for the user. For example, the user in the wine club may be presented with a set of recommendations based on their user level model 114 of which wines the user should purchase in their next wine club delivery.

The platform 100 may include (or interact with) one or more web servers capable of presenting recommendations and other information resulting from the application of the user level models 114 for a user 120. Data from the user level models 114 may be returned to the front end code for presentation to the user 120. In some embodiments, user level models 114 can be created, for example, to generate the recommended wine data for all active wine club users.

In disclosed embodiments, the DTW alignment models 112 can be used in a DTW alignment use case on the "store" page of a website when a user 120 is operating a web browser to view information associated with a particular wine. For example, the website can be operated to present a set of recommended wines which are not specific to that particular user, but which are specific to the wine currently being viewed by the user 120.

In disclosed embodiments, supervised machine learning may be employed in the form of deep learning models 118 which cluster likes and dislikes. This is considered supervised learning because the inputs are labeled using, e.g., the user's ratings. Some models involve unsupervised machine learning, such as, for example, when a model is used to retrieve all of the wines and determine how the data clusters in n-dimensional space. There are no labels applied to these inputs and the learning, therefore, is considered unsupervised.

Figure 2:
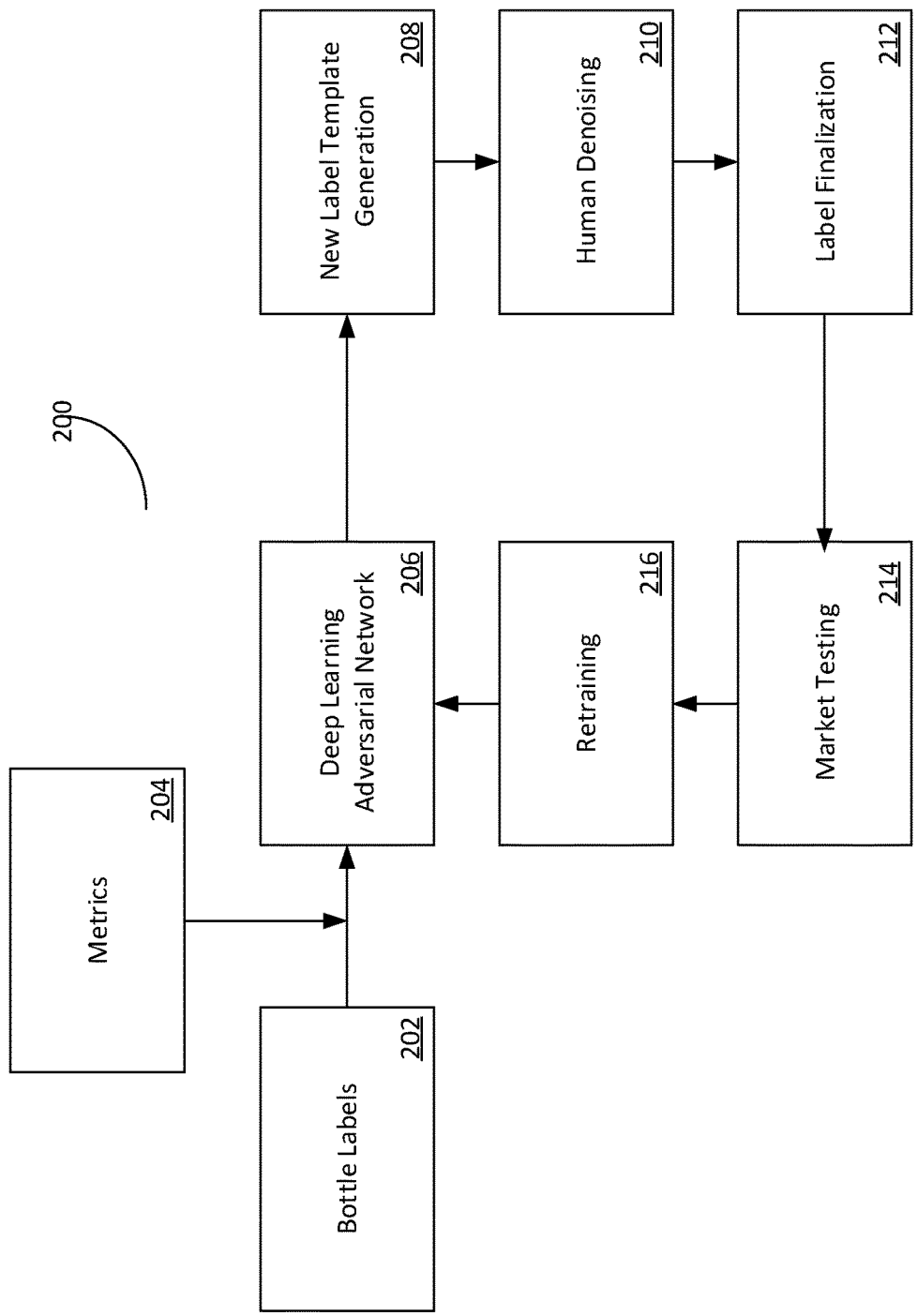
FIG. 2 is a diagram depicting generation of wine labels using machine learning processes.

Reference is now made to FIG. 2 which is a diagram depicting a method 200 of generating consumable product labels using machine learning. In the illustrative, but not limiting, embodiment to be described in conjunction with FIG. 2, the consumable product is wine, and the labels are wine bottle labels. Those skilled in the art, upon reading this disclosure, will appreciate that the process 200 may be used to generate product labels for other consumables as well with desirable results. In disclosed embodiments, there may be semi-supervised machine learning in which some metrics are applied to early data. For example, a model can be trained on data relating to product labels (i.e., physical labels, as opposed to "labeled" data used in machine learning) along with some metrics, e.g., partial labels, with a percentage of likes received from customers and possibly some chemistry data. The algorithm can build the model by learning what makes a good label and a bad label, e.g., in the context of wine labels. The trained model can be queried for a new California red and the algorithm can use deep learning models to generate a noisy template of what a label would look like and its characteristics, e.g., color, font, shape, etc. This can be used as a foundation for completing a final label for a bottle.

In disclosed embodiments, a generative adversarial network (GAN) may be trained on classified data and later used to generate probabilities of features given a specific classification. If there were a sufficient number of labels and enough metrics to allow the algorithm to learn what makes a good label for a red wine, a white wine, a California red wine, etc., then the algorithm could generate label templates which could be used as the basis for a new label. Algorithms could also be used to determine what makes a "bad label," e.g., a label which results in negative ratings during A/B testing in which two bottles of the same wine are given different labels to evaluate the appeal of the label. For example, with enough learning, the algorithm could learn what font size is good for a particular flavor profile.

In disclosed embodiments, wine bottle labels 202 can be used to build a data set, which might be filtered with respect to a particular region of interest. Additional metrics 204 may be added, such as, for example, ratings, SKU performance, seasonal performance (e.g., winter versus summer label performance), and the chemistry of the wine. The data set is used as an input to a generative adversarial network 206 which Applicants believe is desirable to a classifier model as the generative adversarial network 206 allows the algorithm to make things, rather than just classifying things. The generative adversarial network 206 produces a new label template 208 by generating features of high probability as identified by the model. In some situations, such high probability features result in a "noisy" template (which may require human denoising 210). The generated template 208 may define specific characteristics of a desirable label, such as, for example, color (e.g., blue), font type, size, and color, label background texture, placement of text. Denoising at 210 may be performed by a user, e.g., by shifting elements, sketching of the actual text to be used on the label, and performing label finalization 212. One or more versions of the label may be produced and compared to existing labels that have not been doing well so market testing 214 can be used, e.g., A/B testing. For example, the market testing may identify the most desirable labels, the least desirable labels and labels in between. The resulting data can be fed back into the learning network to retrain the algorithm at 216. As more labels are made by this process, or by hand, the algorithm will develop a greater depth of knowledge of how to generate desirable wine labels. In disclosed embodiments, there may be feed forward generation of data, application of denoising, collection of market data to label the results, i.e., in the supervised machine learning sense, and return them as inputs to the algorithm for retraining.

Figure 3:
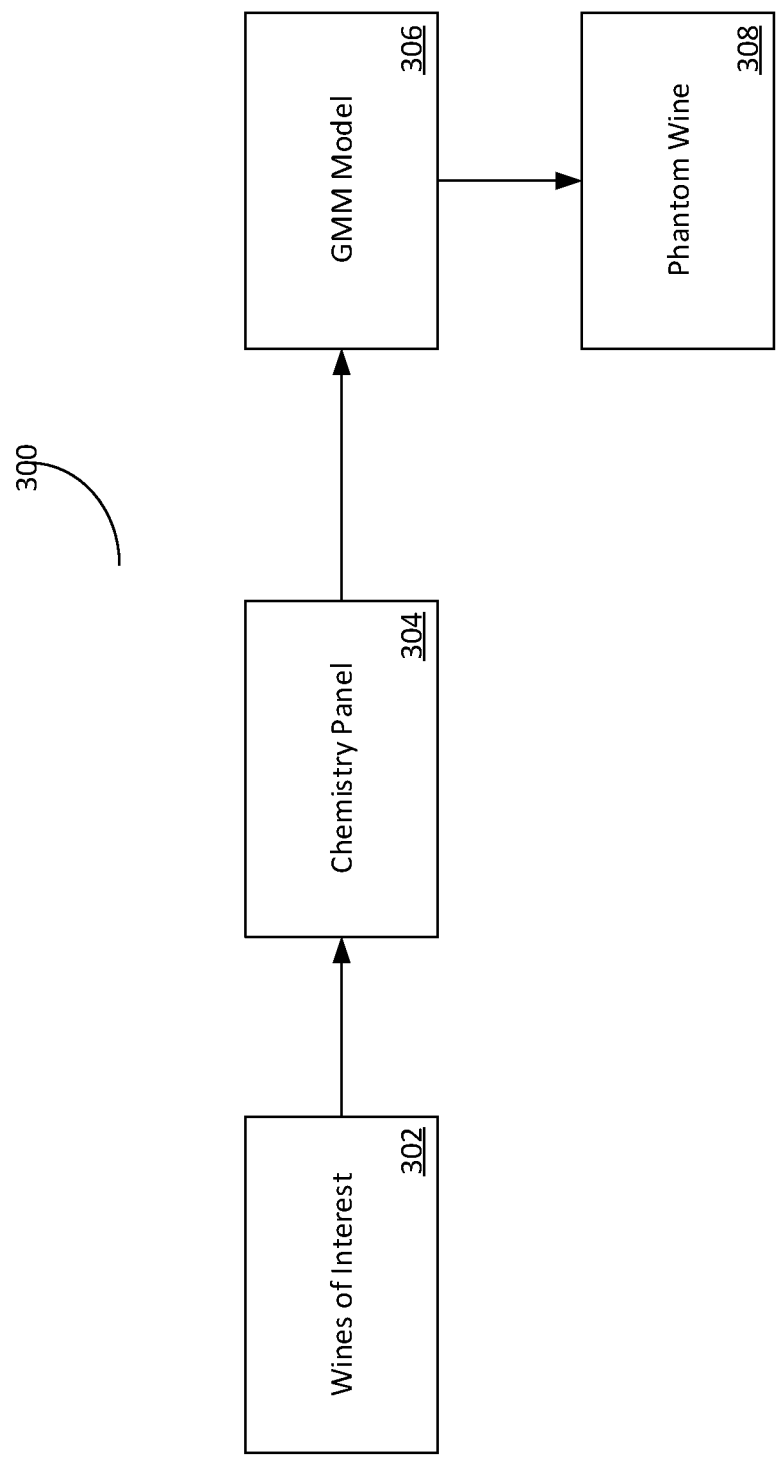
FIG. 3 is a diagram depicting algorithmic wine generation from a set of selected existing wines.

FIG. 3 is a diagram depicting a process 300 for algorithmic consumable product set generation from a set of selected existing consumable products. For clarity and ease of exposition, a specific type of consumable product will be referenced when describing the process 300 of FIG. 3—wine. Those skilled in the art, upon reading the present disclosure, will appreciate that the process 300 may be used with desirable results for other types of consumable products. Pursuant to some embodiments, data associated with a set of wines of interest 302 are analyzed (as described above in conjunction with FIG. 1) to create a specific distribution of chemistry in one or more chemistry panels 304. The chemistry panels 304 (or a subset thereof, e.g., such as a subset selected based on user ratings or other criteria) are used as inputs to a GMM model 306 to create a specific distribution of chemistry which will allow the GMM model 306 to generate a novel data point, e.g., a novel wine, that fits within a specific confined distribution of data. In effect, this is sampling of a given parameter space to obtain a set of representative parameters within a defined parameter space. For example, the GMM model 306 could be used to obtain a good representative top ten wine in California. The result may be referred to as an "algorithmic wine," i.e., a mathematical representation of a wine.

In disclosed embodiments, the GMM model 306 may be created based on a request by the wine producer for new SKUs (i.e., products). For example, it may be desirable to produce a new red wine which will fit into the top ten red wines in a particular region. In such a case, a new "phantom wine" 308 can be created which will be different from all of them (i.e., the top ten wines) but will have a representative chemistry of the top ten wines. The result provides a new chemistry panel, which can be reversed through the standardizer 108 (of the platform 100 of FIG. 1) to produce raw chemistry which can be given to production. For example, the result will tell production that a wine is needed with a particular pH, level of citric acid, level of tannin, etc. These are the characteristics that would typically be measured from a wine. The process 300, thus, works backward from the characteristics and seeks to produce a wine that has the desired characteristics. In disclosed embodiments, a typical profile for a wine may have greater than 30 parameters that are highly impactful on the algorithms described above.

In disclosed embodiments, there may be defined sets of wines of interest, e.g., top ten California red wines. A corresponding filter is applied to the chemistry panels to pull in chemical attributes. A GMM model 306 may be built which samples the parameter space and provides a result which fits within the parameter space. The model 306 generates a new feature vector of chemistry, as noted above, which may be referred to as an "algorithmic wine," "phantom wine," or "virtual wine." This defines a wine which, if it existed, would have chemistry that is representative the applied set of criteria based on the wines of interest.

The phantom wine 308 can be fed back to production to attempt to produce the hypothetical wine. For example, there may be a bulk juice in a tank as a starting point, and the blend chemists, wine makers, etc., try to shift chemistry match the data provided by the algorithm. Chemical sampling can be performed iteratively to produce full feature vectors in the various wine making steps so that, for example, the juice can be sampled, then the first blend, second blend, etc., to see how close they are to the target vector representing the phantom wine. The proximity to the target vector would be measured by application of DTW with the goal of achieving an alignment cost of zero.

The characteristics of the juice are dependent on the particular grape, as well as the particular mash process, and these affect the chemistry of the juice. A winemaker could specify the starting point in terms of parameters such as the grape and initial processes. Samples of the wine can be sent out at any step to obtain a chemistry panel to ascertain the value of parameters such as alcohol content, sugar level, pH, so that adjustments can be made. For example, sugar can be added, more acid can be added to adjust pH, fermentation can be extended to increase alcohol level, etc. In the blending process, there may be two somewhat finished products which may be blended to produce a new finished product based on chemical analysis of the components and the blended result. There may be sampling after bottling to ascertain the effects of the bottling process. In this way, a new wine can be produced from a target which is entirely digital, as opposed to something that is being tasted.

In disclosed embodiments, a phantom wine 308 might be produced, e.g., one generated from a few positive ratings from a user, and used in a DTW alignment to known wines, i.e., existing wines, to obtain the next best choice relative to the phantom wine. In disclosed embodiments, phantom wines may be used in statistical analysis, e.g., projection models which might be used to create simulated orders, e.g., seasonal orders, and to generate market trends forecasts.

Figure 4:
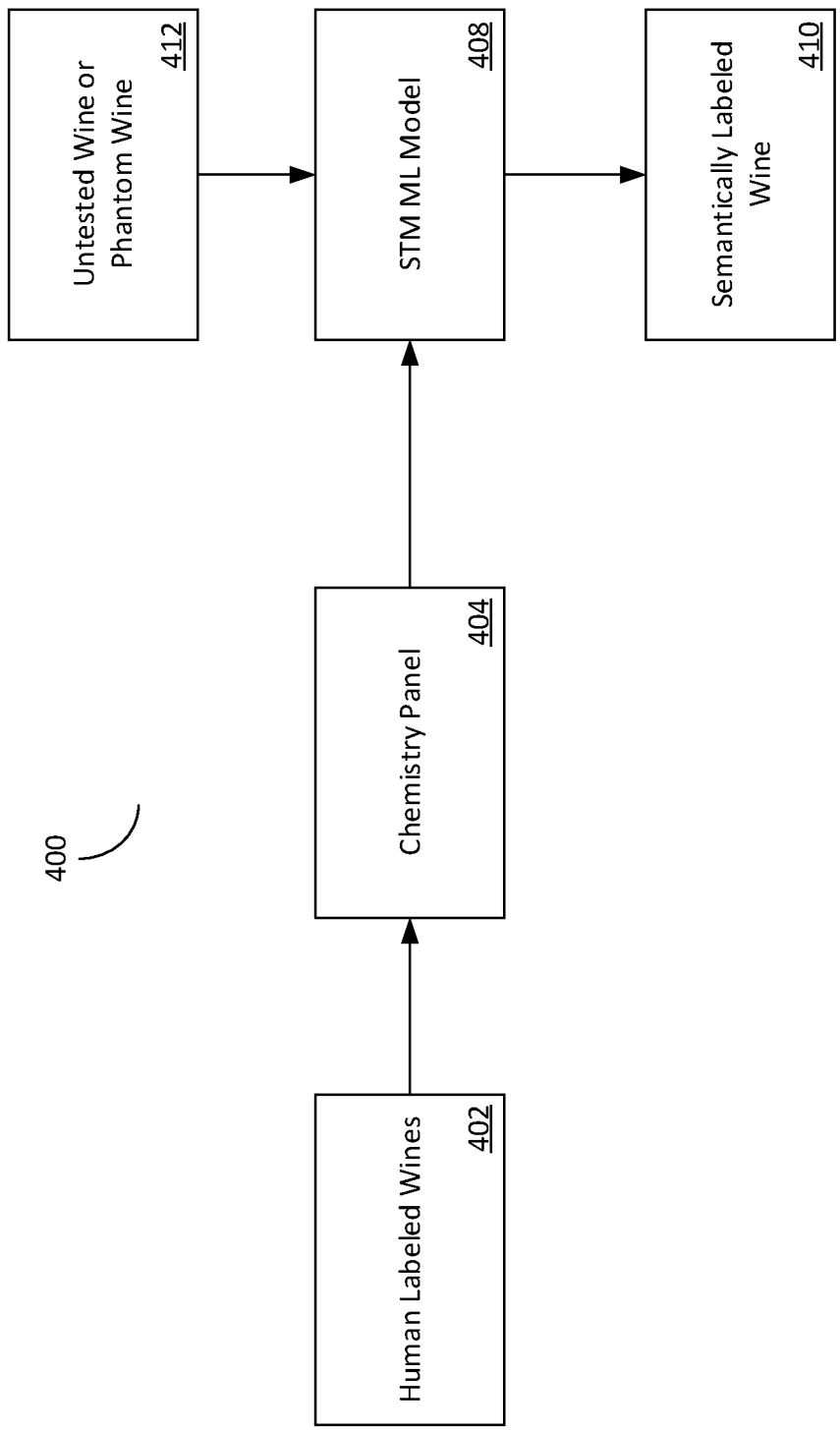
FIG. 4 is a diagram depicting an algorithm for performing semantic translation of a chemical model of a phantom wine.

Reference is now made to FIG. 4, which is a diagram depicting a process 400 for performing semantic translation of a chemical model of a phantom wine (where the model is referred to herein as an "STM"). Conventionally, wine recommendations may be based on tasting by a wine expert who may qualitatively evaluate the characteristics of a wine using terminology, such as, for example, full bodied, spicy, earthy, etc. Such terms are inherently qualitative and subjective. Moreover, to date such labels could only be generated for physically existing wines that may be tasted by a qualified human. Pursuant to some embodiments, the STM approach described herein allows for human tasting metrics to be applied to algorithmic, or digitally-existing, wines.

In disclosed embodiments, the process begins at 402 where the wine produced by a wine maker may be systematically evaluated by wine experts in qualitative terms based on a defined panel of metrics, e.g., body, spiciness, earthiness, tannin level, oak level, etc., on a scale of, e.g., one to five. The evaluated wines are referred to as "human labeled wines" 402. The experts may taste the final products and use this rubric to score the wines and store the results in a database. In disclosed embodiments, qualitative labels obtained in this manner are used to label the chemistry (e.g., the chemistry panels 404 stored in a database) of the wines in a supervised machine learning algorithm. The resulting model trained in this manner becomes a semantic translation model 408 which may be, for example, a machine learning regressor which learns the chemistry of the qualitative taste metrics. This allows the platform to evaluate a wine which has not been tasted, e.g., a phantom wine 412, or an existing wine from which chemistry panels have been obtained but which has not yet been tasted.

Alternatively, the platform 100 may evaluate a wine for which qualitative metrics have been obtained from a wine taster (the human labeled wines 402 or the qualitative metrics used in training the model 408) with the object of evaluating the accuracy of a different wine taster. Moreover, the tested wine taster may be a customer and the accuracy data used to learn the offset of the customer taste profile from that of the given wine expert. The resulting offset could be applied as customer weight in making predictions for that customer using STM 408.

In disclosed embodiments, chemistry data for a wine (the chemistry panel 404) is fed into the model 404 and the output is a semantically-labeled wine 410. Thus, the algorithm goes from chemistry to a rubric of body, spiciness, tannin, etc. It has been found that the algorithm does this with much higher accuracy than can be obtained consistently by expert wine tasters. For example, the algorithm may be given an accuracy range of plus or minus one out of five and there will be very few mistakes. Wine tasters, on the other hand, may be allowed an accuracy range of plus or minus two out of five, which allows for large variations. These techniques allow algorithmic wines to be labeled with qualitative tasting metrics without having someone taste the wines. Also, it allows for the evaluation of wine experts to gauge the accuracy and variance of their pallet. Moreover, the algorithm provides for the chemical composition of a wine to be translated into terminology with which the consumer may be more familiar.

Figure 5:
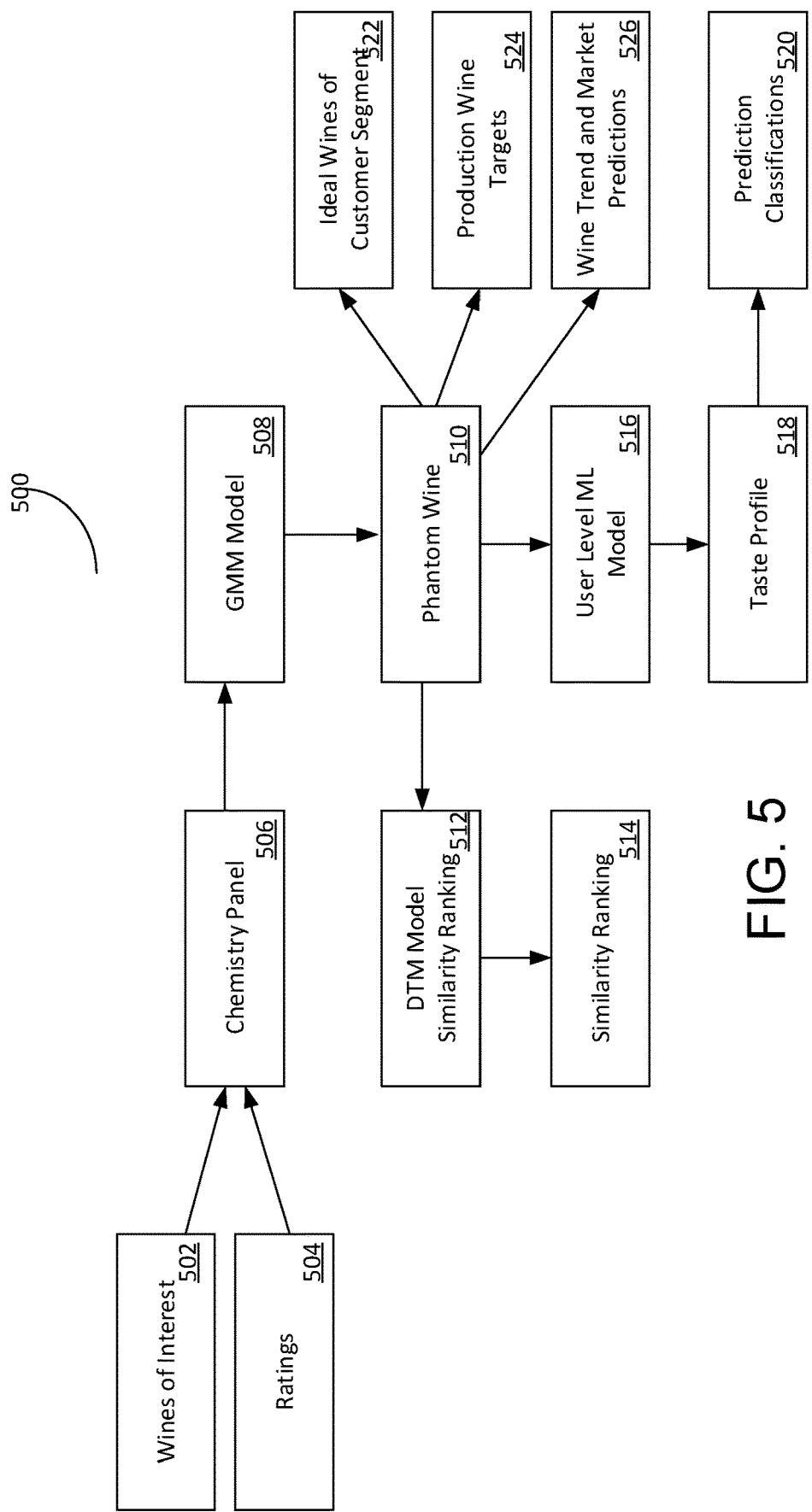
FIG. 5 is a diagram depicting implementation of algorithmic wine generation in the control platform.

FIG. 5 is a diagram depicting a process 500 for algorithmic wine generation in the control platform 100 of FIG. 1. As explained above, wines of interest 502, ratings 504, and other metrics can be applied to chemistry panels 506 to produce a phantom wine 510 using, for example, a GMM model 508. In disclosed embodiments, the phantom wine 510 is aligned to existing wines in the collection using, for example, a DTW model 512. This would allow generation of a list of similarly ranking wines, e.g., the top five, or the top five most distant wines (i.e., an inverse top five list). The phantom wine 510 could also be used to seed user level machine learning models 516. For example, a user has a few likes and only one dislike, more dislikes (which may be phantom wines that fit within the desired profile) can be generated and seeded into the user level model 516 to provide a more informative and accurate machine learning model. This allows a taste profile 518 to be produced for the user which can be used in the generation of probabilities for the prediction of classifications 520 of wines the user will like or dislike.

In disclosed embodiments, a seeded user level model can feed analytics relating to projections and/or simulations to look at wine trends and generate market forecasts 526. Based on this information, phantom wines can be generated which fit particular criteria, e.g., a "winter red" or "winter white." The prebuilt user level models can be used to make classifications of the phantom wines and see what percentage of active users would like the projected, i.e., phantom, wine. Such information can be used to make market and seasonal trend predictions and production wine targets 524 (e.g., how well a phantom wine would be expected to sell). In disclosed embodiments, user level models and generated phantom wines can be used to analyze specific customer segments 522 to identify hypothetical wines which would appeal to the customers in the identified segment. The hypothetical wines could be existing wines in the collection, e.g., determined by applying a DTW model, or phantom wines which might later be developed into actual wines.

Figure 6:
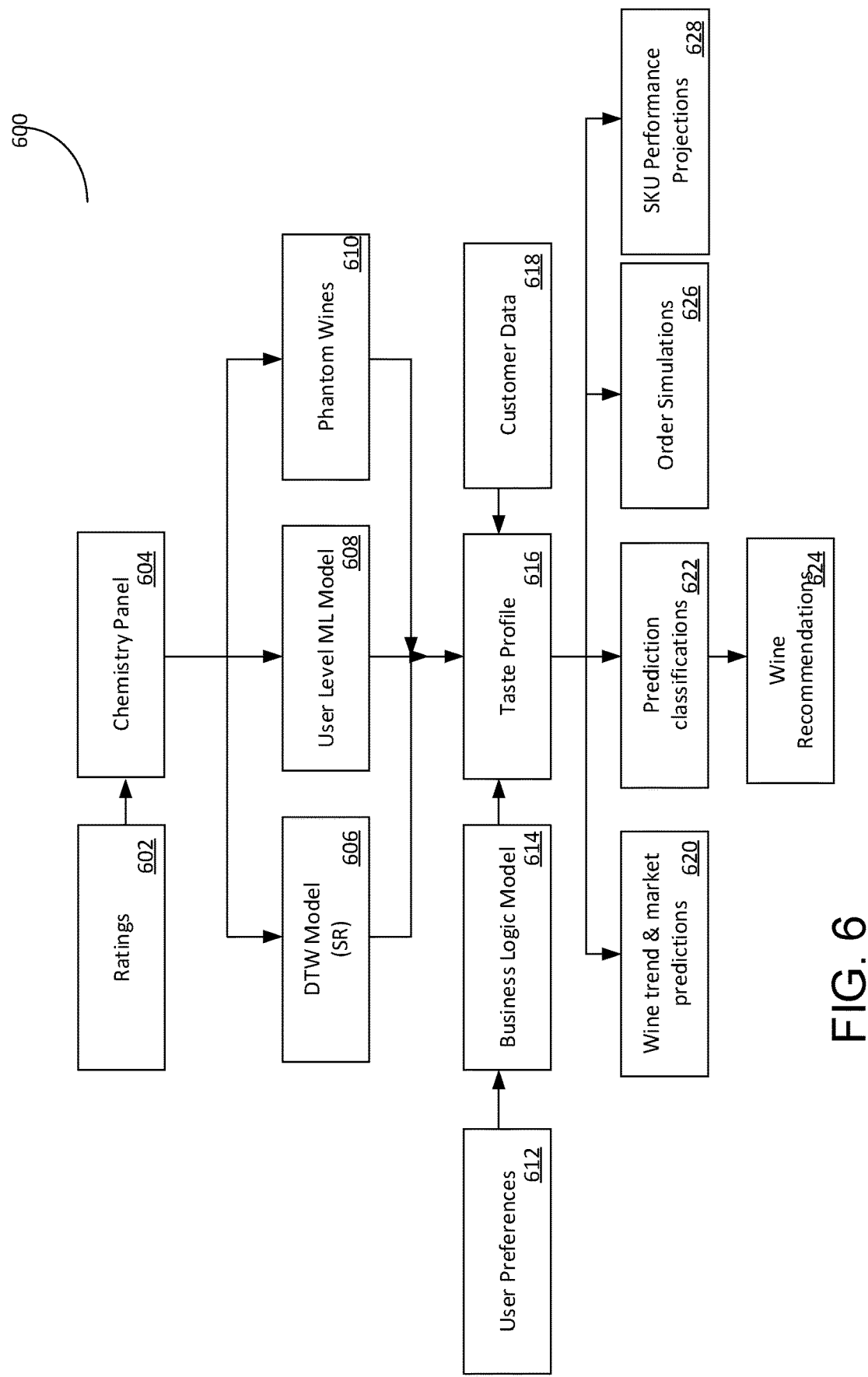
FIG. 6 is a diagram depicting user level modeling for taste profile generation in the control platform.

FIG. 6 is a diagram depicting a process 600 for user level modeling for taste profile generation in the control platform 100 of FIG. 1. In disclosed embodiments, a front end, e.g., a website, may call an API endpoint with a user ID to retrieve the user's ratings 602, which can be associated with particular chemistry panels 604 (e.g., chemistry panels associated with the wines rated by the user). An algorithm (e.g., the paths algorithm) may be implemented at a layer below the chemistry panel layer to make decisions on what can be done with the ratings data associated with the particular user, i.e., what sort of processes can be implemented with sufficient support from the user ratings data 602. For example, a determination can be made as to whether there is enough data to build a full machine learning model 608. In other words, is there sufficient quantity and diversity of user ratings to build a model which will have sufficient accuracy for practical implementation in a commercial website. It may be useful to build a DTW model 606 in cases in which, for example, the user has only one positive ranking. It may be useful to build phantom wines 610 for a user. A combination of such approaches may be used, with the goal of using these techniques to, in effect, enhance the existing user data so that it can be used in training a user level model comparable to those available to users with a sufficient quantity and diversity of ratings. For example, a set of phantom wines 610 and rankings from DTW models 606 can be used to build a machine learning classifier which can provide a taste profile 616 for the user, e.g., a path diagram of the taste of the user in terms of the chemistry. For example, for a particular user, it may be determined whether a particular chemistry parameter (e.g., acetic acid) above or below a determined value, which then causes a specific branching in the decision tree. The resulting classifier is, in effect, a taste profile 616 for the user.

In disclosed embodiments, the user has defined preferences 612, e.g., the user may not want any white wines or international wines, which are fed into models built for business logic. The business logic models 614 may include, for example, data relating to marketing requirements, production requirements, inventory levels, and how soon a duplicate wine can be sent to a customer. The business logic models 614 can be used to apply filters and weights to the user's taste profile 616. This allows prediction of desirable classifications 622, generation of wine recommendations 624, and SKU projections 628 (i.e., the expected sales for a particular SKU based on the users' classifications).

Business logic model information 614 also can be used to perform order simulations 626 to determine, for example, when inventory levels will run out for a particular wine. Because the platform algorithm is being used to fill orders, e.g., the boxes for a wine club, the algorithm can, in effect, be run into the future and keep track of how many times a particular wine gets put into a box, downstream of the various tasting, profiling, and classifications performed on the wines. Because this is modeling business logic and business factors there are simulated orders that can be executed and this allows a prediction of when particular SKUs will be depleted. Other types of order simulations may be used to determine how long it will take to move a quantity of product having a particular SKU, e.g., a particular bottle of wine, out of a warehouse to make room for new products. Other types of order simulations may be used to ensure continued availability of a particular SKU over a defined time period. For example, it may be desirable to ensure that a supply of Beaujolais Nouveau, which cannot easily be replenished, will last until the end of November and, moreover, will be completely depleted by that same date. The learned parameters from these simulations can be used to retrain the business logic models 614 to ensure these business needs are met in practice. These techniques can also be used to predict wine trends and market trends going forward.

In some use cases, a user's top predicted wine (e.g., based on the user level model 608) may be in limited supply, or the user may already have received this wine recently. The business logic model 614 applies constraints to particular parameters and a model is built based on these constraints. In such a case, a score for a particular wine may be based at least in part on the current inventory and the most recent time it was delivered. This score may be referred to as a "SendFactor." It is applied to a user's taste profile to obtain a particular score (i.e., prediction probability). For example, for a particular wine the user's taste profile may indicate that there is a 96% confidence that the user will like the wine, because the chemistry fits well within the confines of the user's built model (i.e., user level model 608). In disclosed embodiments, factors from the business logic layer (e.g., inventory level and recent sending to this user) and user preferences are combined with the prediction probability to produce the SendFactor. In disclosed embodiments, vectors are determined based on factors such as inventory level, recentness (i.e., how recently the user received this wine), and user preferences (e.g., "no California whites"). Vector math, e.g., computation of a Hamming distance, is performed to generate a score, which is fed into a model, along with prediction probability, to determine the SendFactor score. The SendFactor is the final ranking to determine, for example, the next six wines to be placed in a user's wine club box.

In disclosed embodiments, SKU predictions 628 may be performed, which are indicative of the performance (e.g., sales) of a product identified by its associated SKU. All predictions and classifications for a user may be stored, e.g., in cloud storage, which includes, for each SKU, a rating and associated probability for the predicted rating. This data can be pulled into memory, data for SKUs of interest can be retrieved, and determine the predictions for all users for each selected SKU. This could be compared to historic data for the SKU.

In disclosed embodiments, order simulations 626 may be performed, which are indicative of orders which can be expected to occur in the future based on real time conditions. Ratings may be run through the platform to obtain predictions and then an entire order of boxes may be filled, e.g., the next set of boxes to be shipped for the wine club. This inherently incorporates SendFactor logic, business logic, and user preferences. SKU performance projections, on the other hand, are upstream and based on raw user classification data. SKU performance projections, which are essentially just prediction probabilities, to order simulations (i.e., post-SendFactor calculations) to see how that changes things. For example, there might be a prediction that a particular SKU is a hot selling SKU because a lot of users have a high probability of liking it but it may be the case that the business is not getting this SKU to customers in sufficient quantity. This may be due, for example, to low inventory of the product in high-impact warehouses. This situation can be addressed by taking steps to increase inventory or by adjusting the parameters of the SendFactor model, for example by perturbing business logic weights for the SKU, to help distribute the product in the desired manner.

In disclosed embodiments, price data, seasonality, and demographics may be used to supplement the chemistry profile data. In wine club models, pricing data may not be impactful because there are fixed prices. In a website store, the visual aspects of wine bottle labels, price, and user demographics may be incorporated into order simulations for increased accuracy.

Figure 7:
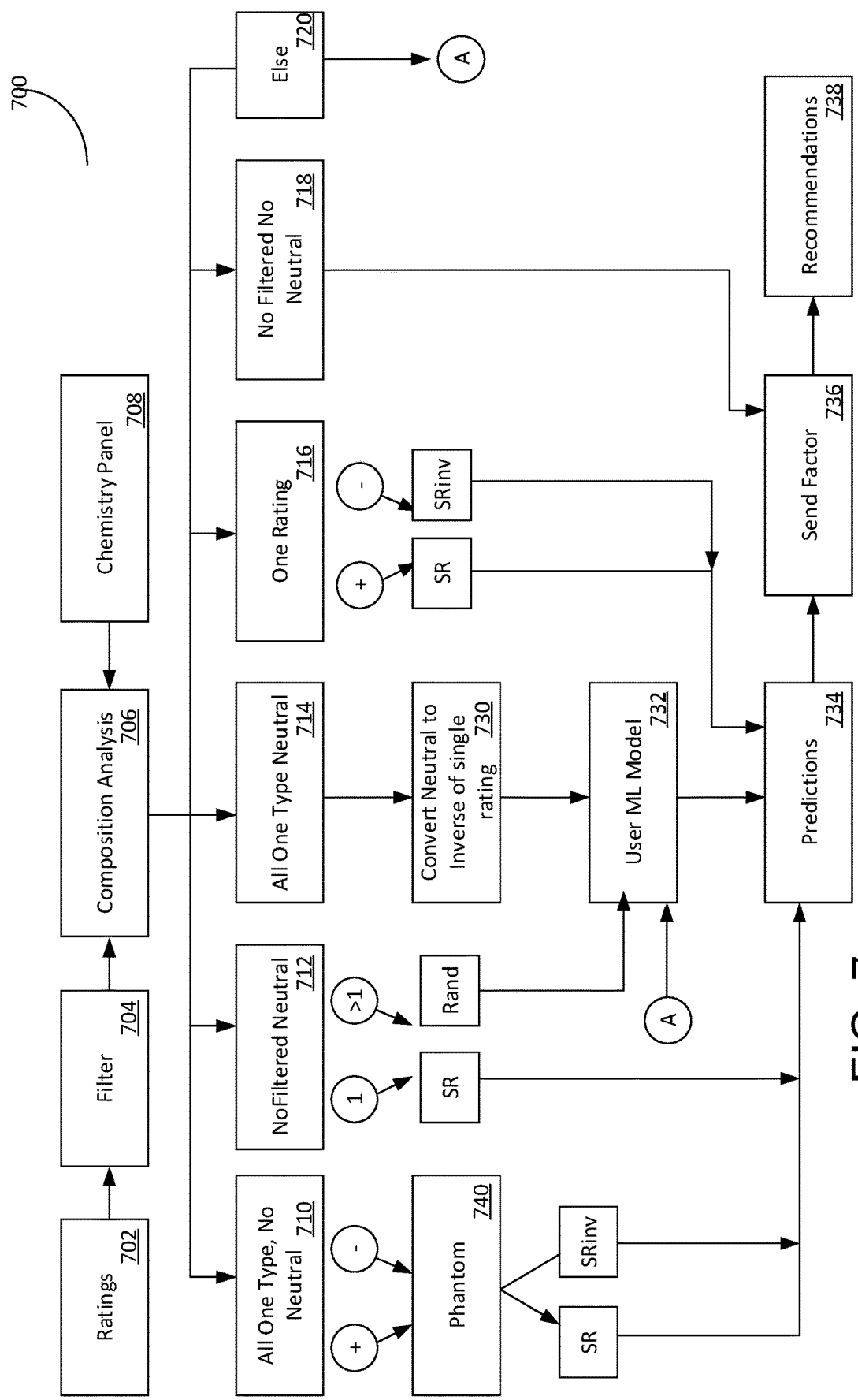
FIG. 7 is a diagram depicting an overview of a paths algorithm.

Reference is now made to FIG. 7 which is a diagram depicting a process 700 of a paths algorithm. The paths algorithm may be used to determine a path within the platform 100 of FIG. 1. The path is a flow of the processes to follow to send a recommendation and/or data requests. The path is based at least in part on the specific data which is available, e.g., user ratings 702, and consideration of how models might be built based on the available data. For example, DTW models and/or GMM models may be used under certain conditions to bootstrap to get the most effective data back to the requestor (such as the user 120 of FIG. 1), even if only minimal data is available (e.g., to handle a "cold start" problem). As explained above, the DTW models take in standardized chemistry vectors and create alignment between the vectors. The integration of the various model types afforded by the paths algorithm makes it possible to, for example, create a chemistry vector with a GMM model and calculate an alignment to actual existing products, e.g., wines, thereby allowing rank data (referred to herein as "spatial ranking" or "SR") to be produced from the alignment.

In disclosed embodiments, if a user does not have a lot of ratings, e.g., the user has five ratings which are all positive or all negative and thus do not provide a sufficient distribution to know the user's taste, the DTW models and GMM models can be used to build out a richer profile, i.e., a model for the user's preferences. This may be considered to be a "bootstrapping" to address "cold start" of the user level model, e.g., for new or infrequent customers.

In disclosed embodiments, the DTW models and GMM models are used frequently by the website, for example, to provide recommendations in situations in which the user has not submitted enough ratings of the products to provide sufficient basis for product selection. In disclosed embodiments, if the user has only one rating, and it is a positive rating, then processing flows through 716 (following the positive rating path) and a DTW model may be used to produce a ranking so the website can offer a group of the next most similar products as recommendations 738. In disclosed embodiments, if the user has only one rating, and it is a negative rating, then processing flows through 716 (following the negative rating path) and a generated ranking may be inverted so the website can offer a group of products which are, in a sense, the opposite of the product given the negative rating. The group of products are provided as a recommendation at 738.

In disclosed embodiments, if the user has a few ratings of the same type of products then a GMM model may be built (following paths 710 or 714). For example, if a user has three negative ratings, then a GMM model may be used to calculate a "negative wine" (e.g., as a phantom at 740), or a wine which is expected to receive a negative rating from the user due to its similarity to the wines given a negative rating by the user. A DTW model can then be built based on the GMM "negative wine" model, and the result can be inverted to identify a group of wines which are likely to appeal to the user.

As shown in FIG. 7, the user's ratings 702 are filtered 704 based upon available chemistry panel data 708 and processed in a compositional analysis 706 to determine the distribution of usable ratings, i.e., ratings of SKUs for which chemistry is known. If a user has filtered ratings of a single type (i.e., positive or negative) with no neutral ratings, processing follows the path starting at 710 and then a phantom wine 740 is generated using a GMM model based on the positive ratings or negative ratings. If the phantom wine 740 is a "good choice," i.e., based on positive ratings, a single rating (SR) process is used to determine a ranking, e.g., by applying a DTW model, and find a number of close wines from the single good phantom wine. This makes it possible to make predictions 734 for the user, which leads to the offering of recommendations 738 after a SendFactor 736 is applied. If the phantom wine 740 is a "bad choice," i.e., based on negative ratings, an inverse spatial ranking ($SR_{inverse}$) process is used to determine a ranking, e.g., by applying a DTW model, and find a number of wines which are farthest from the single bad phantom wine. Again, predictions 734 are made, leading to recommendations 738.

If a user has no filtered positive/negative ratings, i.e., only neutral ratings, and there is only one rating, the processing flows through path 712 and a spatial ranking (SR) process is used to generate predictions, as described above. If, on the other hand, there are more than one neutral rating, then a randomized process is applied to the ratings to produce a skewed set of ratings in which, for example, 80% are positive and 20% are negative. Alternatively, as opposed to random assignment of positive and negative ratings, the neutral ratings may be clustered into two groups using K-Means (with k=2) and assigning a positive rating label to ratings belonging to the larger cluster and negative rating label to the ratings belonging to the other cluster. The resultant adjusted ratings are input to the standard user level mode 7321, e.g., to train a machine learning classifier, to produce predictions 734. If a user has filtered positive/negative ratings which are all of one type, i.e., all positive or all negative, and the ratings include one or more neutral ratings, the processing flows through path 714 and the neutral ratings are converted to the opposite rating label as those of the existing single rating type, and the result is input to the standard user level model 732 so that predictions 734 can be made, leading to recommendations 738.

If a user has only one filtered rating, which is either positive or negative, then processing flows through path 716 and a spatial ranking (SR) process or an inverse spatial ranking ($SR_{inverse}$) process, respectively, is used to determine a ranking. In the case of a single positive rating, a DTW model is applied to find wines close to the single positively-rated wine. In the case of a single negative rating, a DTW model is applied to find wines farthest from the single negatively-rated wine. The resultant rankings are used to produce predictions 734. If a user has no filtered positive/negative ratings and no neutral ratings, then processing flows through path 718 and predictions are not made. Recommendations 738 may be made based on the SendFactor 736 computed in the absence of a prediction percentage, i.e., based solely on factors from the business logic layer (e.g., inventory level and recent sending to this user) and user preferences. The remaining scenario is one where the user ratings are of an adequate distribution of both positive and negative ratings for which chemistry is known, representing the ideal scenario. In this case, processing flows through the path starting at 720 and the standard user level model 732 is relied upon to generate predictions 734 of the unaltered user ratings. As with all other scenarios except when no usable ratings exist after filtering, the prediction probabilities are input to the SendFactor 736 algorithm and recommendations 738 are generated.

The above embodiments may be implemented in hardware, in a computer program executed by a processor, in firmware, or in a combination of the above. A computer program may be embodied on a computer readable medium, such as a storage medium or storage device. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

Figure 8:
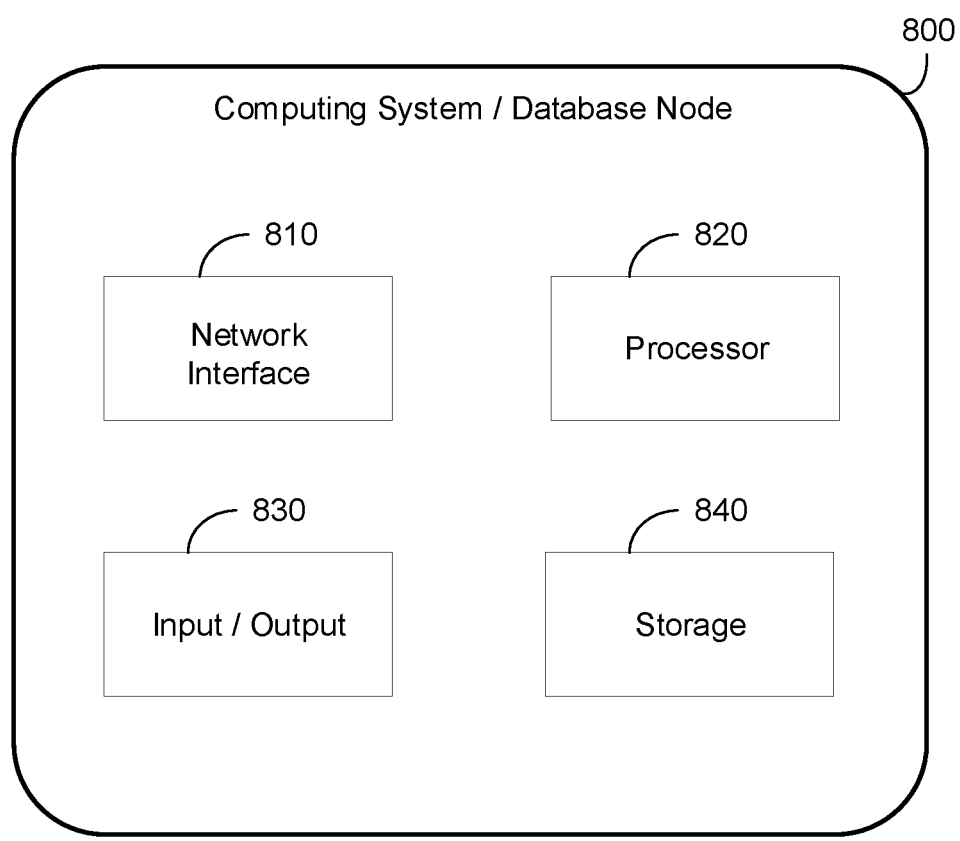
FIG. 8 is a diagram illustrating a computing system for use in the example embodiments described herein.

A storage medium may be coupled to the processor such that the processor may read information from, and write information to, the storage medium. In an alternative, the storage medium may be integral to the processor. The processor and the storage medium may reside in an application specific integrated circuit ("ASIC"). In an alternative, the processor and the storage medium may reside as discrete components. For example, FIG. 8 illustrates an example computing system 800 which may represent or be integrated in any of the above-described components, etc. FIG. 8 is not intended to suggest any limitation as to the scope of use or functionality of embodiments described herein. The computing system 800 is capable of being implemented and/or performing any of the functionality set forth hereinabove.

The computing system 800 may include a computer system/server, which is operational with numerous other general purpose or special purpose computing system environments or configurations. Examples of well-known computing systems, environments, and/or configurations that may be suitable for use as computing system 800 include, but are not limited to, personal computer systems, server computer systems, thin clients, thick clients, hand-held or laptop devices, tablets, smart phones, databases, multiprocessor systems, microprocessor-based systems, set top boxes, programmable consumer electronics, network PCs, minicomputer systems, mainframe computer systems, distributed cloud computing environments, databases, and the like, which may include any of the above systems or devices, and the like. According to various embodiments described herein, the computing system 800 may be an analysis platform (such as shown in FIG. 1), a server, CPU, or the like configured to perform a function as described herein.

The computing system 800 may be described in the general context of computer system-executable instructions, such as program modules, being executed by a computer system. Generally, program modules may include routines, programs, objects, components, logic, data structures, and so on that perform particular tasks or implement particular abstract data types. The computing system 800 may be practiced in distributed cloud computing environments where tasks are performed by remote processing devices that are linked through a communications network. In a distributed cloud computing environment, program modules may be located in both local and remote computer system storage media including memory storage devices.

Referring to FIG. 8, the computing system 800 is shown in the form of a general-purpose computing device. The components of computing system 800 may include, but are not limited to, a network interface 810, one or more processors or processing units 820, an output 830 which may include a port, an interface, etc., or other hardware, for outputting a data signal to another device such as a display, a printer, etc., and a storage device 840 which may include a system memory, or the like. Although not shown, the computing system 800 may also include a system bus that couples various system components including system memory to the processor 820.

The storage 840 may include a variety of computer system readable media. Such media may be any available media that is accessible by computer system/server, and it may include both volatile and non-volatile media, removable and non-removable media. System memory, in one embodiment, implements the processes described herein. The system memory can include computer system readable media in the form of volatile memory, such as random access memory (RAM) and/or cache memory. As another example, storage device 840 can read and write to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, storage device 840 may include at least one program product having a set (e.g., at least one) of program modules that are configured to carry out the functions of various embodiments of the application.

As will be appreciated by one skilled in the art upon reading this disclosure, aspects of the present application may be embodied as a system, method, or computer program product. Accordingly, aspects of the present application may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present application may take the form of a computer program product embodied in one or more computer readable medium(s) having computer readable program code embodied thereon.

Although not shown, the computing system 800 may also communicate with one or more external devices such as a keyboard, a pointing device, a display, etc.; one or more devices that enable a user to interact with computer system/server; and/or any devices (e.g., network card, modem, etc.) that enable computing system 800 to communicate with one or more other computing devices. Such communication can occur via I/O interfaces. Further, computing system 800 can communicate with one or more networks such as a local area network (LAN), a general wide area network (WAN), and/or a public network (e.g., the Internet) via network interface 810. As depicted, network interface 810 may also include a network adapter that communicates with the other components of computing system 800 via a bus. Although not shown, other hardware and/or software components could be used in conjunction with the computing system 800. Examples include, but are not limited to: microcode, device drivers, redundant processing units, external disk drive arrays, RAID systems, tape drives, and data archival storage systems, etc.

According to various embodiments, the computing system 800 may generate data that can be used to predict or determine which consumable (such as wine) a user may enjoy based on data associated with a known consumable. In general, the computing system 800 may be used to implement any of the processes or analyses described elsewhere herein.

As will be appreciated based on the foregoing specification, the above-described examples of the disclosure may be implemented using computer programming or engineering techniques including computer software, firmware, hardware or any combination or subset thereof. Any such resulting program, having computer-readable code, may be embodied or provided within one or more non-transitory computer-readable media, thereby making a computer program product, i.e., an article of manufacture, according to the discussed examples of the disclosure. For example, the non-transitory computer-readable media may be, but is not limited to, a fixed drive, diskette, optical disk, magnetic tape, flash memory, semiconductor memory such as read-only memory (ROM), and/or any transmitting/receiving medium such as the Internet, cloud storage, the internet of things, or other communication network or link. The article of manufacture containing the computer code may be made and/or used by executing the code directly from one medium, by copying the code from one medium to another medium, or by transmitting the code over a network.

The computer programs (also referred to as programs, software, software applications, "apps", or code) may include machine instructions for a programmable processor, and may be implemented in a high-level procedural and/or object-oriented programming language, and/or in assembly/machine language. As used herein, the terms "machine-readable medium" and "computer-readable medium" refer to any computer program product, apparatus, cloud storage, internet of things, and/or device (e.g., magnetic discs, optical disks, memory, programmable logic devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal that may be used to provide machine instructions and/or any other kind of data to a programmable processor.

The above descriptions and illustrations of processes herein should not be considered to imply a fixed order for performing the process steps. Rather, the process steps may be performed in any order that is practicable, including simultaneous performance of at least some steps. Although the disclosure has been described regarding specific examples, it should be understood that various changes, substitutions, and alterations apparent to those skilled in the art can be made to the disclosed embodiments without departing from the spirit and scope of the disclosure as set forth in the appended claims.

We claim:

1. A computer-implemented method, the method comprising:
receiving chemistry panels associated with at least one consumable item, each chemistry panel being associated with and identifying chemical attributes of one of the at least one consumable items, the chemical attributes represented by associated quantitative chemical data values;
building a plurality of different executable machine learning models, each of the plurality of machine learning models being trained on a subset of the received chemistry panels associated with the at least one consumable items;
storing the plurality of trained machine learning models in a storage memory;
receiving an indication of a selection of one or more of the at least one consumable items, the indication of the selection representing an interest of a user;
executing of at least one of the plurality of trained machine learning models using the received indication of the selection of one or more of the at least one consumable items and at least a second subset of the received chemistry panels associated with the at least one consumable items as inputs to the at least one trained machine learning model execution to generate an output derived from the second subset of the received chemistry panels, wherein the plurality of different executable machine learning models includes at least one of a Gaussian Mixture Model (GMM) to generate an algorithmic consumable item and the at least one of the plurality of trained machine learning models execute d is the GMM, wherein an input thereto is the second subset of the received chemistry panels and the GMM is to generate a new algorithmic consumable item that fits within a distribution of chemistry determined for the second subset of the received chemistry panels; and transmitting a result set based on the generated output to the user.

2. The method of claim 1, wherein the at least one consumable item is wine, including bottles of wine distributed via at least one of a website, a physical store, and a wine club.

3. The method of claim 1, wherein each consumable item is identified by a stock keeping unit (SKU) and each of the received chemistry panels is associated with one of the SKUs.

4. The method of claim 1, wherein the received chemistry panels associated with the at least one consumable items are subjected to a standardization process prior to being used in building the plurality of different executable machine learning models.

5. The method of claim 1, wherein the plurality of different executable machine learning models further includes at least one of a Dynamic Time Warping model to determine how different the chemistry panels for the consumable items are from each other, a user level model to provide a recommendation to the user, and a deep learning model to perform at least one function based on the chemistry panels.

6. The method of claim 1, wherein the input to the GMM is a subset of the second subset of the received chemistry panels determined based on a user input criteria.

7. A system comprising:
a processor;
a storage device; and
a memory in communication with the processor, the memory storing program instructions, the processor operative with the program instructions to perform the operations of:
receiving chemistry panels associated with at least one consumable item, each chemistry panel being associated with and identifying chemical attributes of one of the at least one consumable items, the chemical attributes represented by associated quantitative chemical data values;
building a plurality of different executable machine learning models, each of the plurality of machine learning models being trained on a subset of the received chemistry panels associated with the at least one consumable items, the indication of the selection representing an interest of a user;
storing the plurality of trained machine learning models in the storage device;
receiving an indication of one or more of the at least one consumable items;
executing at least one of the plurality of trained machine learning models using the received indication of one or more of the at least one consumable items and at least a second subset of the received chemistry panels associated with the at least one consumable items as inputs to the at least one trained machine learning model execution to generate an output derived from the second subset of the received chemistry panels, wherein the plurality of different executable machine learning models includes at least one of a Gaussian Mixture Model (GMM) to generate an algorithmic consumable item and the at least one of the plurality of trained machine learning models executed is the GMM, wherein an input thereto is the second subset of the received chemistry panels and the GMM is to generate a new algorithmic consumable item that fits within a distribution of chemistry determined for the second subset of the received chemistry panels; and transmitting a result set based on the generated output to a user.

8. The system of claim 7, wherein the at least one consumable item is wine, including bottles of wine distributed via at least one of a website, a physical store, and a wine club.

9. The system of claim 7, wherein each consumable item is identified by a stock keeping unit (SKU) and each of the chemistry panels is associated with one of the SKUs.

10. The system of claim 7, wherein the received chemistry panels associated with the at least one consumable hems are subjected to a standardization process prior to being used in building the plurality of different executable machine learning models.

11. The system of claim 7, wherein the plurality of different executable machine learning models further includes at least one of a Dynamic Time Warping model to determine how different the panels of chemicals for the consumable items are from each other, a user level model to provide a recommendation to the user, and a deep learning model to perform at least one function based on the of the received chemistry panels.

12. The method of claim 7, wherein the input to the GMM is a subset of the second subset of the received chemistry panels determined based on a user input criteria.

* * * * *